United States Patent [19]

Cerami et al.

[11] Patent Number: 5,096,703

[45] Date of Patent: * Mar. 17, 1992

[54] METHOD AND AGENTS FOR PREVENTING STAINING OF TEETH

[75] Inventors: Anthony Cerami, Shelter Island; Michael A. Yamin, New York, both of N.Y.

[73] Assignee: The Rockefeller University, New York, N.Y.

[*] Notice: The portion of the term of this patent subsequent to Jul. 19, 2005 has been disclaimed.

[21] Appl. No.: 605,786

[22] Filed: Oct. 30, 1990

Related U.S. Application Data

[60] Division of Ser. No. 149,726, Jan. 29, 1988, Pat. No. 4,978,684, which is a continuation-in-part of Ser. No. 119,958, Nov. 13, 1987, Pat. No. 4,908,446, which is a continuation-in-part of Ser. No. 798,032, Nov. 14, 1985, Pat. No. 4,758,583, which is a continuation-in-part of Ser. No. 590,820, Mar. 19, 1984, Pat. No. 4,665,192.

[51] Int. Cl.$^5$ .............................. A61K 7/22
[52] U.S. Cl. .............................. 424/54
[58] Field of Search .............................. 424/54

[56] References Cited

U.S. PATENT DOCUMENTS

| 3,055,882 | 9/1962 | Mull | 540/451 |
|---|---|---|---|
| 3,055,883 | 9/1962 | Mull | 540/593 |
| 3,098,066 | 7/1963 | Mull | 540/470 |
| 3,101,336 | 8/1963 | James et al. | 544/402 |
| 3,178,433 | 4/1965 | Mull | 544/398 |
| 3,506,680 | 4/1970 | Berger et al. | 514/632 |
| 3,681,504 | 8/1972 | Johnston et al. | 514/632 |
| 4,665,192 | 5/1987 | Cerami | 424/9 |
| 4,758,583 | 7/1988 | Cerami et al. | 514/399 |
| 4,978,684 | 12/1990 | Cerami et al. | 514/632 |

FOREIGN PATENT DOCUMENTS

| 64-56614 | 3/1989 | Japan . | |
| 809165 | 6/1956 | United Kingdom | 514/632 |

OTHER PUBLICATIONS

Bain, M. J. Chlorhexidine in dentistry—a review. *New Zealand Dental Journal*, 76, 49-54.

Bunn, H. F. et al. Further identification of the nature & linkage of the carbohydrate in hemoglobin A$_{Ic}$ *Biochem. & Biophys. Res. Comm.*, 67(1), 1975, 103-109.

Brownlee, M. et al. Aminoguanidine prevents diabetes-induced arterial wall protein cross-linking, *Science*, 232, 1986, 1629-1632.

Brownlee, M. et al. Nonenzymatic glycosylation & the pathogenesis of diabetic complications. *Ann. Int. Med.*, 101, 1984, 527-537.

Brownlee, M. et al. Covalent attachment of soluble proteins by nonenzymatic glycosylated collagen, *J. Exp. Med.*, 158, 1983, 1739-1744.

Eble, A. S. et al. Nonenzymatic glucosylation & glucose-dependent cross-linking of protein. *J. Biol. Chem.*, 238, 1983, 9406-9412.

(List continued on next page.)

*Primary Examiner*—Prince E. Willis
*Assistant Examiner*—Jerry D. Johnson
*Attorney, Agent, or Firm*—Klauber & Jackson

[57] ABSTRACT

The present invention relates to methods and agents for preventing the staining of teeth caused by the nonenzymatic browning of proteins in the oral cavity. Both oral and parenteral administration of the agents are disclosed. Suitable agents for the inhibition of nonenzymatic browning may be formulated as rinses and toothpastes, and include compounds capable of reacting with the carbonyl moiety of the early glycosylation product resulting from the initial reaction of a target protein in the nonenzymatic browning reaction. Preferred agents are those having an active nitrogen-containing substituent, as well as amino acids, their esters and amides. These preparations may further include known antiplaque agents such as chlorhexidine.

13 Claims, 1 Drawing Sheet

OTHER PUBLICATIONS

Godfrey, L. A. *The Synthesis of Heterocyclic Compounds from Urea Derivatives*. Doctoral Dissertation, U. of London, 1962.

Hull, P. S. Chemical inhibition of plaque. *J. Clin. Periodont.*, 7, 1989, 431–442.

Monnier, V. M. et al. Accelerated age-related browning of human collagen in diabetes mellitus, *Proc. Natl. Acad. Sci. U.S.A.*, 81, 1984, 583–587.

Pongor, S. et al. Aging of proteins: Isolation & identification of a fluorescent chromophore from the reaction of polypeptides with glucose. *Proc. Natl. Acad. Sci. U.S.A.*, 81, 1984, 2684–2688.

Tonelli, P. M. et al. Chlorhexidine: A review of the literature. *J. West. Soc. Periodont.*, 31(1), 1983.

Nordbo, H. Ability of chlorhexidine & benzalkonium chloride to catalyze browning reactions in vitro. *J. Dent. Res.*, 58(4), 1979, 1429.

METHOD AND AGENTS FOR PREVENTING STAINING OF TEETH

CROSS REFERENCE TO RELATED APPLICATIONS

This is a division of application Ser. No. 07/149,726, filed Jan. 29, 1988 now U.S. Pat. No. 4,978,684, which is a continuation-in-part of application Ser. No. 119,958, filed Nov. 13, 1987, now U.S. Pat. No. 4,908,446 which is a continuation-in-part of application Ser. No. 798,032, filed Nov. 14, 1985, which is in turn a continuation-in-part of application Ser. No. 590,820, filed Mar. 19, 1984, and now U.S. Pat. No. 4,665,192.

This invention was made in part with government support under Grant Number PHSAM 19655 awarded by the National Institutes of Health. The government has certain rights in the invention.

BACKGROUND OF THE INVENTION

The present invention relates generally the reaction that occurs between glucose and proteins and, more particularly, to the inhibition by various agents of the reaction of nonenzymatically glycosylated proteins leading to advanced glycosylation end products. The nonenzymatic browning reaction which occurs in the oral cavity results in the discoloration of teeth. Presently used anti-plaque agents accelerate this nonenzymatic browning reaction and further the staining of the teeth. The appeal of a perfect smile composed of pearly-white teeth is undeniable. Many dollars are spent to achieve this appearance, and the natural discoloration which occurs on the tooth surfaces often becomes quite noticeable in many individuals. Tooth discoloration is also greatly accelerated in most individuals who use certain anti-plaque agents to prevent oral disease. The purpose of the present invention is to provide a method and agents for preventing the discoloration which occurs on the tooth surface as a result of nonenzymatic browning, both naturally and as a result of the use of anti-plaque agents. As used herein, "tooth" and "teeth" refer to both naturally occurring and artificial teeth, artificial tooth surfaces and restorations.

Dental caries, gingivitis and periodontal disease are widespread and affect nearly all individuals to some extent cosmetically, medically, and financially. These conditions arise from the action of certain microorganisms, principally bacteria, which colonize surfaces in the mouth and whose action lead to demineralization of bone, resulting in caries, and chronic irritation and infection of gum tissue (gingivitis) especially in pockets surrounding the teeth, leading to periodontal disease. The results of both processes can be painful, disfiguring and psychologically debilitating.

The development of tooth and gum disease is a complex process involving contributions from the tooth and gum surface, components and properties of saliva, diet, and the numerous species of bacteria present in the mouth, as well as many other factors. Generally, incubation of a newly cleaned tooth surface in the mouth initially results in the deposition on the surface of a material called pellicle, which is composed of protein and polysaccharide derived from saliva and bacterial cells. As colonizing bacteria grow, they produce a polysaccharide from the decomposition of food sugars. This polysaccharide favors the attachment of the bacteria to the tooth surface and also favors mineralization of calcium salts from saliva in the pellicle. As the process continues, the bacterial mass known as plaque becomes a focus for demineralization of bone and irritation of tissues. Acids produced by bacteria during food sugar fermentation dissolve bone, and the plaque mass prevents buffers in saliva from neutralizing these acids. The result is dental caries. The bacteria in plaque and those residing in pockets surrounding teeth produce endotoxin and other well-known bacterial products which are intensely irritating to tissues and cause the tissues to react resulting in recession of gum tissue, demineralization of bone, and localized irritation.

One of the consequences of long-term exposure of proteins in the pellicle and plaque to sugars in the mouth is the process of nonenzymatic browning, which results in discoloration of the tooth surface. Nonenzymatic browning, also known as the Maillard reaction, has been well studied by food chemists since it is responsible for the brown color which forms during the cooking and long-term storage of foods. In this reaction, amino groups in food proteins and other molecules react with sugars to form covalent adducts which undergo rearrangements and result in highly polymerized, colored products. While this process is well-known in food, only recently was its significance realized as concerns the human body and consequences of the long-term exposure of glucose to amino groups on proteins and other macro-molecules in the body. The Maillard reaction in vivo has been studied extensively in the last few years and nonenzymatic browning and cross-linking of proteins in vivo has been shown to be an important mechanism by which the sequelae of diabetes and aging arise (see M. Brownlee et al., "Nonenzymatic glycosylation and the pathogenesis of diabetic complications," *Annals of Internal Medicine*, 101, pp. 527–537 (1986)). Elevated glucose levels in diabetes leads more rapidly to consequences involving permanent cross-linking of proteins, yet the normal glucose levels in non-diabetics eventually leads to the same complications.

Methods to prevent nonenzymatic browning in vivo with agents such as aminoguanidine and other inhibitors have been studied (Brownlee et al., "Aminoguanidine prevents diabetes-induced arterial wall protein cross-linking," *Science*, 232, pp. 1629–1632 (1986)), Cerami et al., U.S. Pat. application Ser. No. 798,032; and U.S. Pat. application Ser. No. 07/119,958.

For many years certain agents have been tested and used to reduce the extent of oral diseases including dental caries, gingivitis and periodontal disease. Regular brushing and flossing apparently are inadequate, at least to the extent practiced by the average individual. Abrasive agents such as silica have been incorporated into toothpastes to attempt to physically remove plaque by enhancing the effectiveness of brushing. Antimicrobial agents have been formulated in oral rinses for regular use to kill bacteria in the mouth. Such agents include sanguinarine, an extract from the bloodroot, which kills certain oral bacteria; certain forms of active peroxide for killing microorganisms; rinses containing alcohol and other ingredients; and, more recently, a class of cationic anti-microbial agents with remarkable anti-plaque properties.

These latter agents, the cationic antiseptics, include such agents as alexidine, cetyl pyridinium chloride, chlorhexidine gluconate, hexetidine, and benzalkonium chloride. Many have been tested for efficacy but one, chlorhexidine gluconate, has shown the greatest promise as an anti-plaque agent of low toxicity (see Hull, "Chemical inhibition of plaque," *J. Clin. Periodontol.*, 7, pp. 431–432 (1980); Bain, "Chlorhexidine in dentistry: A review," *New England Dent. J.*, 76, pp. 49–54 (1980)); Tonelli et al., "Chlorhexidine: A review of the literature," *J. West. Soc. Periodent.*, 31, pp. 5-10 (1983)) and has recently become available in the United States in a prescription formulation known as Peridex ® which contains 0.12% chlorhexidine gluconate in a solution of water, alcohol, glycerine, flavoring, sweetening and coloring agents. Chlorhexidine gluconate, formulated in such a rinse, shows excellent promise as an anti-plaque agent, but it has been found to possess an unfortunate side effect: staining of teeth. While this side effect is of no medical concern, it is an extreme psychologic concern because stained teeth look ugly and project an undesirable image to others. Tooth staining by chlorhexidine and other anti-plaque agents apparently results from the enhancement of the Waillard reaction. Nordbo, *J. Dent. Res.*, 58, p. 1429 (1979) reported that chlorhexidine and benzalkonium chloride catalyze browning reactions in vitro. Chlorhexidine added to mixtures containing a sugar derivative and a source of amino groups underwent increased color formation, attributed to the Maillard reaction. It is also known that use of chlorhexidine results in an increased dental pellicle. Nordbo proposed that chlorhexidine resulted in tooth staining in two ways: first, by increasing formation of pellicle which contains more amino groups, and secondly, by catalysis of the Maillard reaction leading to colored products. Thus, there exists a need for preventing the staining caused by chlorhexidine gluconate and other cationic mouth rinses which will not interfere with their potent anti-microbial and resulting anti-plaque activity.

SUMMARY OF THE INVENTION

In accordance with the present invention, a method of preventing the staining of teeth caused by the nonenzymatic browning of proteins in the oral cavity is disclosed. In particular, agents for the inhibition of nonenzymatic browning are formulated as rinses and toothpaste alone or in combination with known anti-plaque agents such as chlorhexidine. Additionally, the agent can be administered orally or parenterally since it concentrates in the salivary glands and is subsequently secreted into the oral cavity in the saliva.

The agents which can be utilized in the methods and formulations of this invention are those disclosed in our co-pending applications Ser. No. 798,032 and Serial No. 119,958, herein incorporated by reference. Thus, the agents are those capable of reacting with the carbonyl moiety of the early glycosylation product formed by the initial glycosylation of the target protein in the nonenzymatic browning reaction. Preferred agents are those having an active nitrogen-containing substituent. Among these are those wherein the active nitrogen substituent is a hydrazine group. Others are amino acids and their esters and amides.

Specific agents utilizable in the present invention are aminoguanidine, α-hydrazinohistidine, lysine and the substituted aminoguanidine derivatives having the structural formula

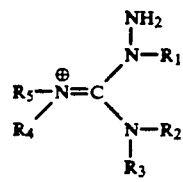

wherein $R_1$ is hydrogen or a lower alkyl group of 1-6 carbon atoms, a hydroxyethyl group, or together with $R_2$ may be a lower alkylene bridge of 2-4 carbon atoms; $R_2$ is hydrogen or a lower alkyl group of 1-6 carbon atoms or together with $R_1$ or $R_3$ is a lower alkylene bridge of 2-4 carbon atoms, amino, hydroxy, or an aminoalkylene group of the formula $$-(CH_2)_n-\underset{R_7}{\underset{|}{N}}-R_6$$

wherein n is an integer of 2-7 and $R_6$ and $R_7$ are independently a lower alkyl group of 1-6 carbon atoms or together with the nitrogen atom are a morpholino or piperidino group; $R_3$ is hydrogen, a lower alkyl group of 1-6 carbon atoms, or together with $R_2$ or $R_4$ is a lower alkylene bridge of 2-4 carbon atoms; $R_4$ is hydrogen, a lower alkyl group of 1-6 carbon atoms or together with $R_3$ is a lower alkylene bridge of 2-4 carbon atoms; or an amino group; $R_5$ is hydrogen, or a lower alkyl group of 1-6 carbon atoms; with the proviso that at least one of $R_1$, $R_2$, $R_3$, $R_4$ or $R_5$ is other than hydrogen; and their pharmaceutically acceptable acid addition salts, and mixtures of the enumerated compounds.

The lower alkyl groups referred to above contain 1-6 carbon atoms and include methyl, ethyl, propyl, butyl, pentyl, hexyl, and the corresponding branched chain isomers thereof.

Certain of the compounds utilizable in the present invention are represented by the formula

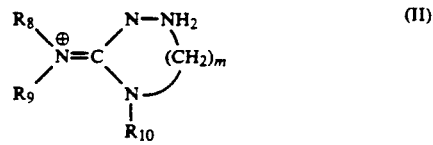

wherein $R_8$, $R_9$ and $R_{10}$ are hydrogen or a lower alkyl group and m is an integer of 2-4. Specifically preferred compounds of formula II are those wherein $R_8$, $R_9$ and $R_{10}$ are both hydrogen and those wherein m=2.

The compounds of this invention appear to react with the glycosylation product thereby preventing the same from later forming the advanced glycosylation end products of nonenzymatic browning which result in the discoloration of the teeth in the oral cavity.

Accordingly, it is a principal object of the present invention to provide a method of inhibiting the discoloration of teeth resulting from nonenzymatic browning in the oral cavity which comprises administration to a subject in need of such therapy an amount effective to inhibit the formation of advanced glycosylation end products of a composition comprising an agent capable of reacting with the carbonyl moiety of the early glycosylation product formed by the initial glycosylation in the nonenzymatic browning reaction.

It is a further object of the present invention to provide agents capable of participating in the reaction with the said early glycosylation products in the method as aforesaid.

It is a still further object of the present invention to provide compositions incorporating agents capable of participating in the reaction with the said early glycosylation products adapted for use in the oral cavity according to the aforesaid method.

Other objects and advantages will become apparent to those skilled in the art from a review of the detailed description which proceeds with reference to the following illustrative drawing.

BRIEF DESCRIPTION OF THE DRAWING

FIG. 1 is a photograph depicting the results of the incubation of gelatin/paper disks with reducing sugars to simulate the environment of a protein-covered tooth surface.

DETAILED DESCRIPTION OF THE PREFERRED EMBODIMENTS

In accordance with the present invention, methods and associated compositions have been developed which are believed to inhibit the discoloration of teeth resulting from nonenzymatic browning in the oral cavity. In particular, the invention relates to a method of inhibiting the discoloration of teeth resulting from nonenzymatic browning in the oral cavity which comprises administration to a subject in need of such therapy an amount effective to inhibit the formation of advanced glycosylation end products of a composition comprising an agent capable of reacting with the carbonyl moiety of the early glycosylation product formed by the initial glycosylation in the nonenzymatic browning reaction.

In accordance with this method, the agents capable of reacting with the carbonyl moiety of the early glycosylation product formed by the initial glycosylation in the nonenzymatic browning reaction are formulated into compositions adapted for use in the oral cavity. Particularly suitable formulations are oral rinses and toothpastes incorporating the active agent.

In the practice of this invention, conventional formulating techniques are utilized with non-toxic, pharmaceutically acceptable carriers typically utilized in the amounts and combinations that are well-known for the formulation of such oral rinses and toothpastes.

The agent capable of reaction with the carbonyl moiety of the early glycosylation product formed by the initial glycosylation in the nonenzymatic browning reaction is formulated in compositions in an amount effective to inhibit the formation of advanced glycosylation end products. This amount will, of course, vary with the particular agent being utilized, but typically is in the range of 0.01% to 1.0%, by weight, of the particular formulation.

Additionally, since the agents of the aforesaid method are concentrated in the salivary glands upon oral ingestion or parenteral administration, they can be so administered. This concentration in the salivary glands results in their secretion into saliva, the net result being that they are functionally placed in the oral cavity where they can effect their desired method. For such administration, the particular agent can be formulated in any conventional oral or parenteral dosage form. A particularly desirable dosage form is the incorporation of the agent into a vitamin tablet or fluoride tablet so as to maximize patient, and particularly juvenile patient, compliance.

Specific agents utilizable in the present invention are aminoguanidine, α-hydrazinohistidine, lysine and the aminoguanidine derivatives encompassed by formulae I and II.

The aminoguanidine derivatives encompassed in formulae I and II are conveniently prepared by chemical syntheses well known in the art. Certain of the compounds encompassed by formula I are known compounds readily available from chemical supply houses and/or preparably by synthetic methods specifically published therefor. The novel compounds of formula II are prepared by analogous routes. For instance, 1,3-diaminoguanidine monohydrochloride and 2-hydrazino-2-imidazoline hydrobromide are available from Aldrich Chemical Company. Acetic acid hydrazide and L-glutamic acid-gamma-hydrazine hydrate can be obtained from Sigma Chemical Company. Methanesulfonyl hydrazide is obtainable from Lancaster Chemical Co. N-hydroxyhydrazinecarboximidamide tosylate can be synthesized according to the procedure of *J. Med. Chem.* 27, 236–238 1984. Likewise, the procedure describing 1-methylhydrazinecarboximidamide tosylate is published in *J. Med. Chem.*, 25, 505–518 (1982). N-(3-dimethylaminopropyl)hydrazinecarboximidamide dihydrobromide hydrate is mentioned in U.S. Pat. No. 4,544,759 (1985).

Other compounds described in the chemical and patent literature and encompassed by formula I are:
N-methylhydrazinecarboximidamide;
N-ethylhydrazinecarboximidamide;
N-propylhydrazinecarboximidamide;
N-butylhydrazinecarboximidamide;
N-hexylhydrazincarboximidamide;
N,N'-dimethylhydrazinecarboximidamide;
N,N'-diethylhydrazinecarboximidamide;
N,N'-diisopropylhydrazinecarboximidamide;
N-(3-diethylaminopropyl)hydrazinecarboximidamide;
N-(2-diethylaminoethyl)hydrazinecarboximidamide;
N-(2-dimethylaminoethyl) hydrazinecarboximidamide;
N-[2-(4-methylpiperazinyl)ethyl]hydrazinecarboximidamide;
N-[2-(1-pyrrolidinyl)ethyl]hydrazinecarboximidamide;
N-[2-(1-piperidinyl)ethyl]hydrazinecarboximidamide;
N-[2-(1-hexahydroazepinyl)ethyl]hydrazinecarboximidamide;
N-[2-(4-methyl-1-hexahydro-1,4-diazepinyl)propyl]-hydrazinecarboximidamide;
N-[2-(1-hexahydroazocinyl)ethyl]hydrazinecarboximidamide;
N-[2-(1-octahydroazoninyl)ethyl]hydrazinecarboximidamide; and
N-[2-(2,4-dimethyl-1-pyrrolidinyl)ethyl]-hydrazinecarboximidamide.

Parent U.S. Ser. No. 119,958 describes the preparation of the novel compounds of formula II.

The following examples detail the methods and compositions utilizable in the present invention.

EXAMPLE 1

To evaluate the ability of inhibitors of nonenzymatic browning to inhibit tooth staining enhanced by cationic anti-plaque agents, in vitro experiments were performed using bovine serum albumin (BSA; concentration, 25 mg/mL) as the test protein undergoing nonenzymatic browning in the presence of the sugar glucose (at 100 mM).

Aminoguanidine hydrochloride was used as the nonenzymatic browning inhibitor, and chlorhexidine gluconate as the anti-plaque agent known to enhance nonenzymatic browning. The latter was in the form of the prescription mouth rinse Peridex ®, in which it is present at a concentration of 0.12% along with certain other inert ingredients including ethanol (11.6%). The final concentration of chlorhexidine in the experimental mixtures was 0.024%, and 11.6% ethanol was used as a control in all mixtures lacking Peridex ®.

Various incubation mixtures containing combinations of the above components were prepared in a 0.5 M phosphate buffer at pH 7.4 containing 3 mM sodium azide to prevent the growth of microorganisms. The mixtures were left at 37° C. for three weeks, after which time the BSA in each mixture was precipitated by the addition of saturated ammonium sulfate solution. The precipitate was washed in saturated ammonium sulfate solution, and the BSA precipitate dissolved in phosphate-buffered saline. The degree of nonenzymatic browning of each BSA sample was determined by measuring relative fluorescence at an excitation wavelength of 370 nm and an emission wavelength of 440 nm. This is a measure of the amount of nonenzymatic browning products present, including furoylfuranylimidazole (Pongor et al., *Proceedings of the National Academy of Sciences of the U.S.A.*, 81, pp. 2684-2688 (1984); U.S. Pat. No. 4,665,192). The amount of BSA in the solution was measured by a standard method and the degree of nonenzymatic browning expressed as fluorescence per milligram of protein.

The composition of the incubation mixtures and the resulting specific fluorescence in two experiments is expressed in the following table. Because fluorescence is measured in relative units in each experiment, values in each experiment may be compared directly but not those between experiments.

TABLE 1

INHIBITION OF NONENZYMATIC BROWNING BY AMINOGUANIDINE

| Incubation Mixture Fluorescence containing BSA and: | Specific Exp. 1 | Exp. 2 |
|---|---|---|
| no addition | 8.5 | 1.3 |
| glucose | 36.0 | 10.0 |
| glucose + chlorhexidine | 59.2 | 17.8 |
| glucose + chlorhexidine + 100 mM aminoguanidine | 15.2 | 2.2 |
| glucose + 100 mM aminoguanidine | 15.0 | 1.7 |

It is clear from these results that the incubation of glucose with BSA results in nonenzymatic browning over the control incubation and the inclusion of chlorhexidine significantly increases the degree of browning. This enhanced browning caused by chlorhexidine is as completely inhibited by the inclusion of aminoguanidine as is the browning reaction without chlorhexidine. These same results were obtained by comparing the visible spectra of the BSA solutions. Thus, aminoguanidine inhibits nonenzymatic browning especially the enhanced nonenzymatic browning caused by chlorhexidine.

EXAMPLE 2

To further study the ability of inhibitors of nonenzymatic browning to prevent the discoloration of protein on a surface, such as that which occurs on the tooth surface, the following surface browning experiment was performed. As a substitute for a pellicle-covered tooth surface, unexposed and developed photographic paper was used to provide a fixed protein (gelatin, i.e., collagen) surface on a paper backing. Five millimeter circles were punched and immersed for one week at 50° C. in a solution of 100 mM glucose-6-phosphate in a 0.5 M phosphate buffer, pH 7.4, containing 3 mM sodium azide. Glucose-6-phosphate is a sugar capable of participating in nonenzymatic browning at a more rapid rate than glucose. In addition to the glucose-6-phosphate, chlorhexidine and/or aminoguanidine were included. After incubation, the gelatin/paper disks were rinsed with water, observed for brown color, and photographed.

Figure 1:
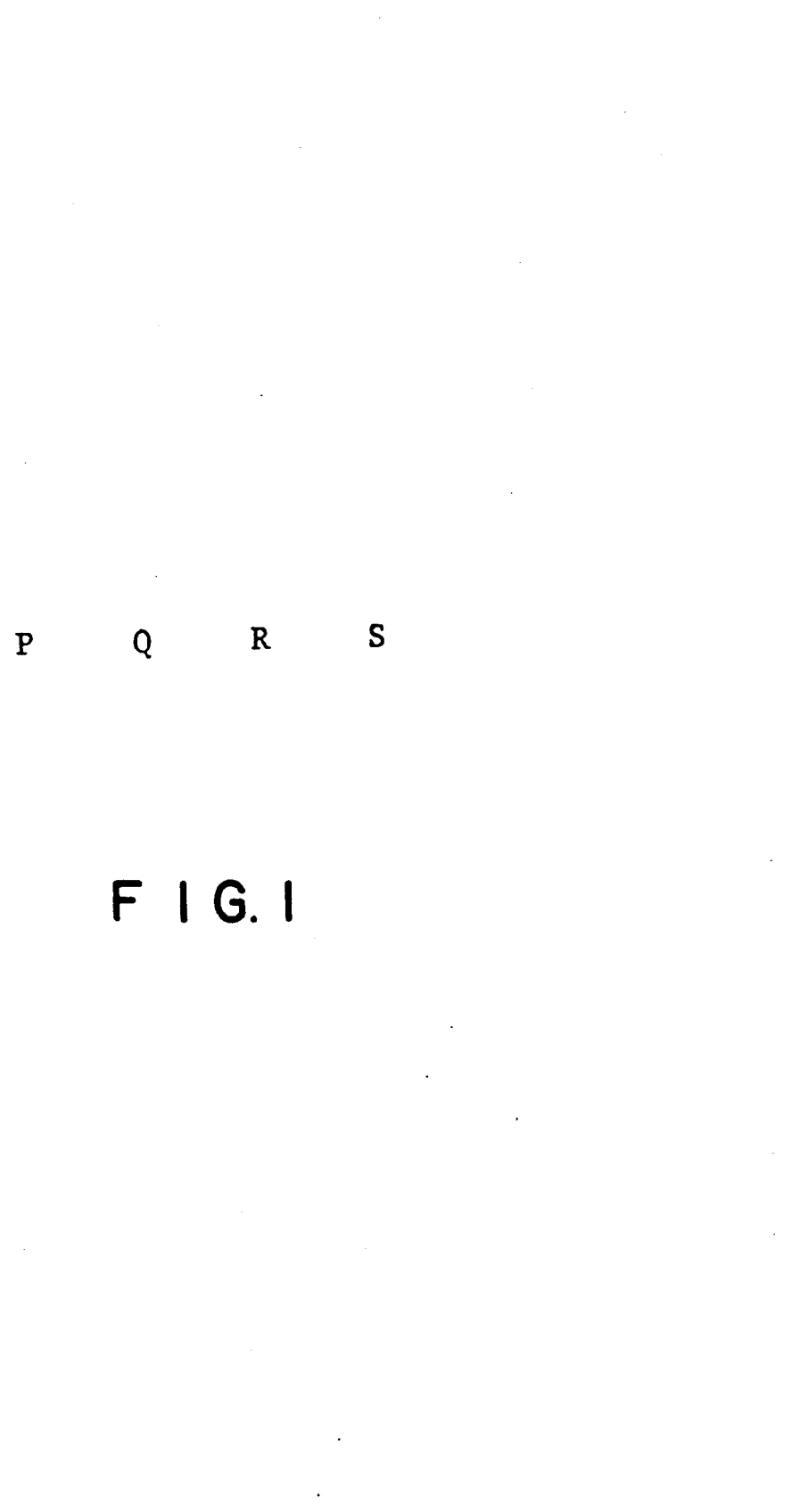

FIG. 1 illustrates the results of one such experiment. Incubation of the disks in glucose-6-phosphate alone (P) showed slight brown color versus disks soaked in buffer alone (not shown). Inclusion of chlorhexidine (in the form of Peridex ®, at a final concentration of 0.04% chlorhexidine) showed significant browning (Q). Addition of aminoguanidine hydrochloride (100 mM) to the chlorhexidine completely inhibited browning of the gelatin (R), as did inclusion of aminoguanidine in the absence of chlorhexidine (S).

The slight brown color formed by the action of glucose-6-phosphate on the gelatin surface alone and its prevention by aminoguanidine demonstrates the utility of the present invention in preventing nonenzymatic browning of tooth surfaces. The enhanced browning in the presence of chlorhexidine and its complete prevention with aminoguanidine demonstrates the utility of the present invention in preventing the anti-plaque agent-enhanced nonenzymatic browning which occurs with chlorhexidine.

EXAMPLE 3

Chlorhexidine is believed to exert its anti-plaque activity by having the ability to stick to the tooth surface and exert anti-microbial activity. The following experiment was performed to ensure that aminoguanidine does not reduce the anti-microbial activity of chlorhexidine.

The K10 strain of *Escherichia coli* was exposed to ten-fold serial dilutions of chlorhexidine (in the form of Peridex ® containing either no addition or a final concentration of 1 mM or 10 mM aminoguanidine hydrochloride. After exposure, bacteria were plated on M63/glucose agar and allowed to grow at 37° C., after which time colonies were counted.

Results showed that aminoguinidine did not reduce the anti-microbial efficiency of chlorhexidine at all dilutions at which inhibition of bacterial growth occurred.

EXAMPLE 4

| Oral Rinse Containing Chlorhexidine and Aminoguandine: | |
|---|---|
| Aminoguanidine | 1.4% |
| Chlorhexidine gluconate | 0.12% |
| Ethanol | 11.6% |
| Sodium saccharin | 0.15% |
| FD&C Blue No. 1 | 0.001% |
| Peppermint Oil | 0.5% |
| Glycerine | 10.0% |
| Tween 60 | 0.3% |
| Water to | 100% |

| Toothpaste Containing Aminoguanidine: | |
|---|---|
| Aminoguanidine hydrochloride | 5.5% |
| Sorbitol, 70% in water | 25% |
| Sodium saccharin | 0.15% |
| Sodium lauryl sulfate | 1.75% |
| Carbopol 934, 6% dispersion in water | 15% |
| Oil of Spearmint | 1.0% |
| Sodium hydroxide, 50% in water | 0.76% |
| Dibasic calcium phosphate dihydrate | 45% |
| Water to | 10% |

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method of inhibiting the discoloration of teeth resulting from nonenzymatic browning in the oral cavity which comprises administration to a subject in need of such therapy an amount effective to inhibit the formation of advanced glycosylation end products of a composition comprising aminoguanidine and its pharmaceutically acceptable acid addition salts, and mixtures thereof.

2. The method of claim 1, wherein the composition is formulated as an oral rinse.

3. The method of claim 2, wherein the composition additionally contains an anti-plaque agent.

4. The method of claim 3, wherein the anti-plaque agent is chlorhexidine.

5. The method of claim 1, wherein the composition is formulated as a toothpaste.

6. The method of claim 5, wherein the composition additionally contains an anti-plaque agent.

7. The method of claim 6, wherein the anti-plaque agent is chlorhexidine.

8. The method of claim 1, wherein the composition is formulated for oral administration.

9. The method of claim 1, wherein the composition is formulated for parenteral administration.

10. A composition for inhibiting the discoloration of teeth resulting from nonenzymatic browning in the oral cavity which comprises an amount effective to inhibit the formation of advanced glycosylation end products of a composition comprising aminoguanidine and its pharmaceutically acceptable acid addition salts, and mixtures thereof and, an anti-plaque agent, together with a non-toxic, pharmaceutically acceptable carrier therefor.

11. A composition according to claim 10, formulated as an oral rinse.

12. A composition according to claim 10, formulated as a toothpaste.

13. A composition according to claim 10, wherein the antiplaque agent is chlorhexidine.

* * * * *